US005873893A

United States Patent [19]
Sullivan et al.

[11] Patent Number: 5,873,893
[45] Date of Patent: Feb. 23, 1999

[54] METHOD AND APPARATUS FOR VERIFYING THE INTEGRITY OF AN OUTPUT CIRCUIT BEFORE AND DURING APPLICATION OF A DEFIBRILLATION PULSE

[75] Inventors: Joseph L. Sullivan; Lawrence A. Borschowa; Richard C. Nova, all of Kirkland, Wash.

[73] Assignee: Physio-Control Corporation, Redmond, Wash.

[21] Appl. No.: 811,834

[22] Filed: Mar. 5, 1997

[51] Int. Cl.$^6$ ........................................ A61N 1/39
[52] U.S. Cl. ....................................... 607/5; 607/7
[58] Field of Search ................................ 607/5–8

[56] References Cited

U.S. PATENT DOCUMENTS

| | | |
|---|---|---|
| 4,800,883 | 1/1989 | Winstrom . |
| 4,821,723 | 4/1989 | Baker, Jr. et al. . |
| 4,850,357 | 7/1989 | Bach, Jr. . |
| 5,083,562 | 1/1992 | de Coriolis et al. . |
| 5,099,844 | 3/1992 | Faupel . |
| 5,431,684 | 7/1995 | Archer et al. . |
| 5,431,686 | 7/1995 | Kroll et al. . |
| 5,441,518 | 8/1995 | Adams et al. . |
| 5,468,254 | 11/1995 | Hahn et al. . |
| 5,470,341 | 11/1995 | Kuehn et al. . |
| 5,489,293 | 2/1996 | Pless et al. . |
| 5,591,213 | 1/1997 | Morgan . |
| 5,593,427 | 1/1997 | Gliner et al. . |
| 5,601,612 | 2/1997 | Gliner et al. ................ 607/7 |
| 5,607,454 | 3/1997 | Cameron et al. . |
| 5,733,310 | 3/1998 | Lopin et al. ................. 607/7 |

FOREIGN PATENT DOCUMENTS

| | | |
|---|---|---|
| 0 553 864 A2 | 8/1993 | European Pat. Off. . |
| 0 747 093 A2 | 12/1996 | European Pat. Off. . |
| WO 93/16759 | 9/1993 | WIPO . |
| 9427674 | 12/1994 | WIPO ....................... 607/5 |
| WO 94/27674 | 12/1994 | WIPO . |
| WO 95/05215 | 2/1995 | WIPO . |
| WO 95/09673 | 4/1995 | WIPO . |

OTHER PUBLICATIONS

Gust H. Brady et al., "Multicenter Comparison of Truncated Biphasic Shocks and Standard Damped Sine Wave Monophasic Shocks for Transthoracic Ventricular Defibrillation," *Circulation*, vol. 94, No. 10, Nov. 15, 1996, pp. 2507–2514.

Gust H. Brady et al., "Truncated Biphasic Pulses for Transthoracic Defibrillation, " *Circulation*, vol. 91, No. 6, Mar. 15, 1995, pp. 1768–1774.

Richard O. Cummins, M.D., et al., Overview, "Ventricular Fibrillation, Automatic External Defibrillators, and the United States Food and Drug Administration: Confrontation Without Comprehension," *Annals of Emergency Medicine*, vol. 26, Nov. 1995, p. 621.

(List continued on next page.)

*Primary Examiner*—William E. Kamm
*Assistant Examiner*—Carl H. Layno
*Attorney, Agent, or Firm*—Christensen O'Connor Johnson & Kindness PLLC

[57] ABSTRACT

An external defibrillator with a microprocessor for testing the integrity of an output circuit prior to and during the delivery of a multiphasic defibrillation pulse from an energy storage capacitor coupled to the output circuit is disclosed. The output circuit contains a plurality of switches. The integrity of the output circuit and the output switches is determined by selectively monitoring the changes in the voltage level on the energy storage capacitor while certain tests or functions are being performed. A scaling circuit steps down the voltage level of the high-energy storage device so that it can be measured and monitored by the microprocessor. The microprocessor may compensate for the failure of an output switch by locating a usable set of output switches and using them to provide a discharge path through the output circuit for application of a monophasic pulse.

17 Claims, 8 Drawing Sheets

OTHER PUBLICATIONS

Scott A. Feeser, M.D. et al., Abstract, "Strength–Duration and Probability of Success Curves for Defibrillation with Biphasic Waveforms," *Circulation*, vol. 82, 1990, pp. 2128–2141.

Bradford E. Gliner et al., "Transthoracic Defibrillation of Swine with Monophasic and Biphasic Waveforms," *Circulation*, vol. 92, No. 6, Sep. 15, 1995, pp. 1634–1643.

Mark W. Kroll, "A Minimal Model of the Single Capacitor Biphasic Defibrillation Waveform," *PACE*, vol. 17, Nov. 1994, Part I, pp. 1782–1792.

Anthony S.L. Tang, M.D. et al., Abstract, "Ventricular Defibrillation Using Biphasic Waveforms: The Importance of Phasic Duration," *Journal of American College of Cardiology*, vol. 13, 1989, pp. 207–214.

Gregory P. Walcott et al., "Choosing the Optimal Monophasic and Biphasic Waveforms for Ventricular Defibrillation," *Journal of Cardiovascular Electrophysiology*, vol. 6, No. 9, Sep. 1995, pp. 737–750.

METHOD AND APPARATUS FOR VERIFYING THE INTEGRITY OF AN OUTPUT CIRCUIT BEFORE AND DURING APPLICATION OF A DEFIBRILLATION PULSE

FIELD OF THE INVENTION

This invention relates generally to methods and apparatus for monitoring the operation of external defibrillators, and more particularly to a method and apparatus for verifying the integrity of an output circuit of an external defibrillator.

BACKGROUND OF THE INVENTION

One of the most common and life-threatening medical conditions is ventricular fibrillation, a condition where the human heart is unable to pump the volume of blood required by the human body. The usual way of restoring a normal rhythm to a heart experiencing ventricular fibrillation is to apply a strong electric pulse to the heart using an external cardiac defibrillator. External cardiac defibrillators have been successfully used for many years in hospitals by doctors and nurses, and in the field by emergency treatment personnel, e.g., paramedics.

Conventional external cardiac defibrillators first accumulate a high-energy electric charge on an energy storage capacitor. When a switching mechanism is closed, the stored energy is transferred to a patient in the form of a large current pulse. The current pulse is applied to the patient via a pair of electrodes positioned on the patient's chest. The switching mechanism used in most contemporary external defibrillators is a high-energy transfer relay. A discharge control signal causes the relay to complete an electrical circuit between the storage capacitor and a wave shaping circuit whose output is connected to the electrodes attached to the patient.

Although the high-energy transfer relays used in external cardiac defibrillators have performed satisfactorily, they have a variety of disadvantages. One of the major disadvantages is the electromagnetic interference (EMI) that is caused when the relay is closed. EMI can be detrimental to the signals used by nearby control circuits and makes the use of EMI-sensitive circuitry impractical during the application of the defibrillation pulse. Due to the EMI interference, external defibrillators typically temporarily place all control circuitry in an "inactive" state while a defibrillation pulse is applied. External defibrillators are therefore unable to verify that the switching mechanism or relay is working properly because a limited amount of circuitry is operational during the application of the defibrillation pulse.

An additional disadvantage of using a relay is that prior to the application of the defibrillation pulse, it may be impractical to test the integrity of the relay. For example, one method for testing the relay requires discharging the energy storage capacitor into a test load. This and similar methods require not only discharging most of the energy in the energy storage capacitor during each test, but also require extra circuitry including a test load.

The present invention is directed to providing a method and apparatus that overcome the foregoing and other disadvantages. More specifically, the present invention is directed to providing a method and apparatus for verifying the integrity of an output circuit before and during the application of a defibrillation pulse.

SUMMARY OF THE INVENTION

An external defibrillator having an output circuit that is controlled by a microprocessor is provided. The output circuit includes several solid-state switches through which a defibrillation pulse is discharged to a patient from an energy storage device, preferably an energy storage capacitor. Prior to application of the defibrillation pulse, the integrity of each of the switches in the output circuit is verified. The integrity of the output circuit during the application of a defibrillation pulse is also verified by monitoring the changing charge level of the energy storage capacitor.

In accordance with one aspect of the invention, the output circuit is a circuit having four legs arrayed in the form of an "H" (hereinafter the "H-bridge"). Each leg of the output circuit contains a solid-state switch. By selectively switching on pairs of switches in the H-bridge, a biphasic defibrillation pulse may be applied to a patient. Prior to application of the defibrillation pulse, each of the legs in the output circuit is checked by switching the switches on in a desired order while the energy storage capacitor is partially charged.

In accordance with another aspect of the invention, the integrity of the H-bridge is monitored during application of the defibrillation pulse by periodically measuring the voltage across the energy storage capacitor. A voltage outside an expected range may indicate the failure of the H-bridge.

In accordance with still another aspect of the invention, a failed leg in the H-bridge is compensated for by identifying a pair of legs that provides a conductive path between the energy storage capacitor and the patient. If an operational pair of legs is identified, the defibrillator delivers a monophasic, rather than a biphasic, defibrillation pulse. The current or duration of the monophasic pulse may also be altered by changing the charge on the energy storage capacitor.

In accordance with yet another aspect of the invention, a scaling circuit is provided to step down the voltage across the energy storage capacitor so that it can be measured by the microprocessor. The scaling circuit is adjustable to allow the microprocessor to measure various voltage ranges across the energy storage capacitor.

In accordance with another aspect of the invention, if any error is detected before or during delivery of the defibrillation pulse, an error handling routine may be called to analyze and attempt to compensate for the indicated failure. The error handing routine generates a visual, aural, or other warning to the user to indicate that the defibrillator is not functioning properly. The warning to the user is especially advantageous under circumstances where the user might not otherwise be aware that the defibrillator is not functioning properly.

It will be appreciated that the disclosed method of testing the output circuit is advantageous in that it allows the integrity of the output circuit and connection to the patient to be checked both before and during the application of a defibrillation pulse. Providing a monophasic pulse in the present invention has a distinct advantage in that it allows a defibrillation pulse to be delivered to the patient even when part of the output circuit has failed. Moreover, the use of a scaling circuit allows the high voltages of the energy storage capacitor to be measured by the microprocessor for control of the defibrillator in real time.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
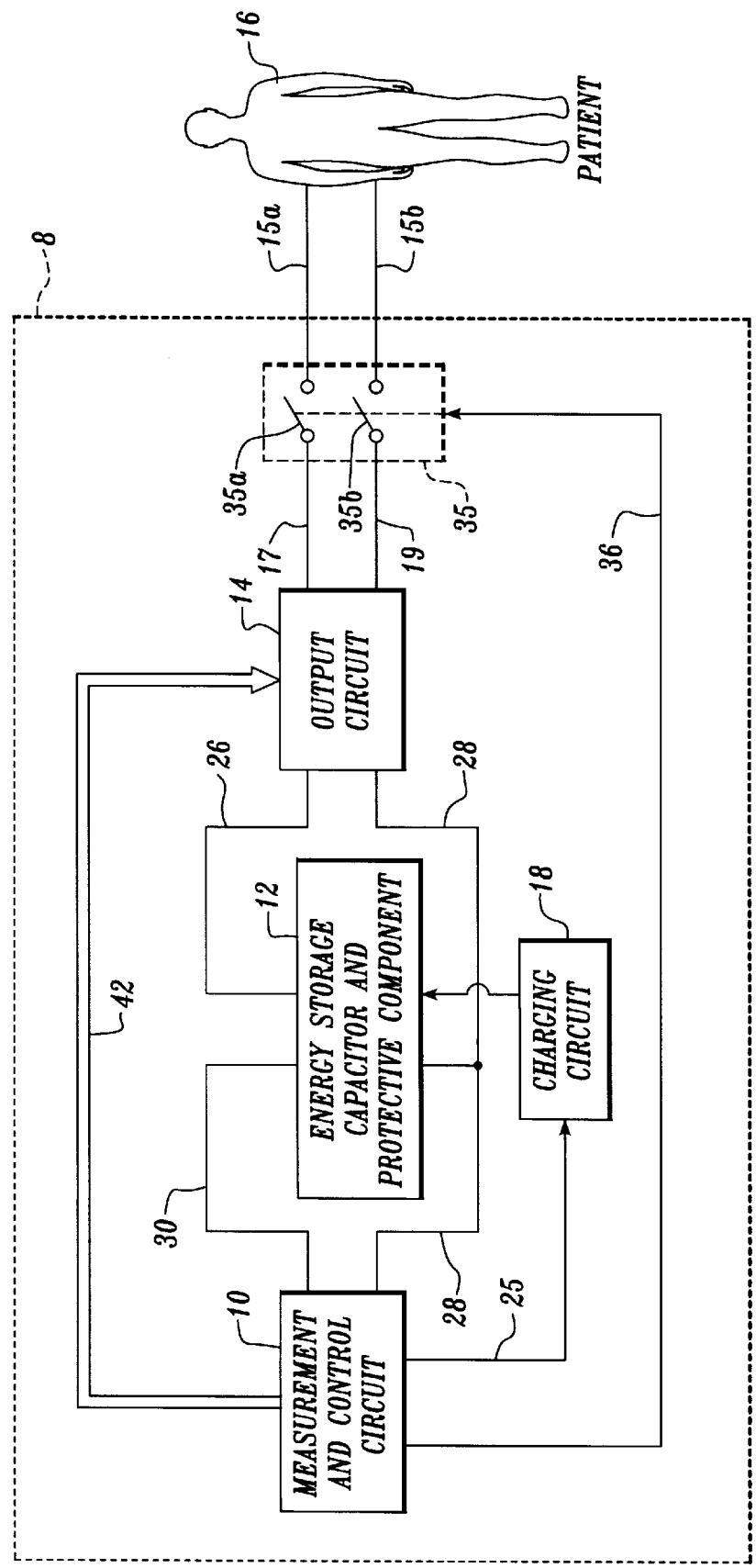
FIG. 1 is a block diagram of an external defibrillator having an output circuit that is tested before and during an application pulse in accordance with the present invention.

FIG. 1 is a block diagram of an external defibrillator 8 that is connected to a patient 16. The defibrillator includes a measurement and control circuit 10 that is connected to an energy storage capacitor and protective component 12 via a charging circuit 18. During the operation of the defibrillator, the measurement and control circuit 10 controls the charging circuit 18 via a control line 25 to charge the energy storage capacitor to a desired voltage level. Feedback on the voltage level of the energy storage capacitor is provided to the measurement and control circuit 10 on a pair of lines 28 and 30.

After charging to a desired level, the energy stored in the energy storage capacitor may be delivered to the patient 16 in the form of a defibrillation pulse. The energy storage capacitor and protective component 12 is connected by lines 26 and 28 to an output circuit 14. The measurement and control circuit 10 is connected to the output circuit 14 by a control bus 42 and to a patient isolation relay 35 by a control line 36. Application of appropriate control signals over the control bus 42 and control line 36 causes the output circuit 14 to conduct energy from the energy storage capacitor. The energy is delivered to the patient 16 attached to the defibrillator 8 over a set of electrodes 15a and 15b. The electrode 15a is attached to an apex line 17 in output circuit 14 through a switch 35a in the patient isolation relay. The electrode 15b is attached to a sternum line 19 in output circuit 14 through a switch 35b in the patient isolation relay. In a manner described in greater detail below, the measurement and control circuit 10 verifies the integrity of the output circuit 14 before and during the transfer of the defibrillation pulse.

Figure 2:
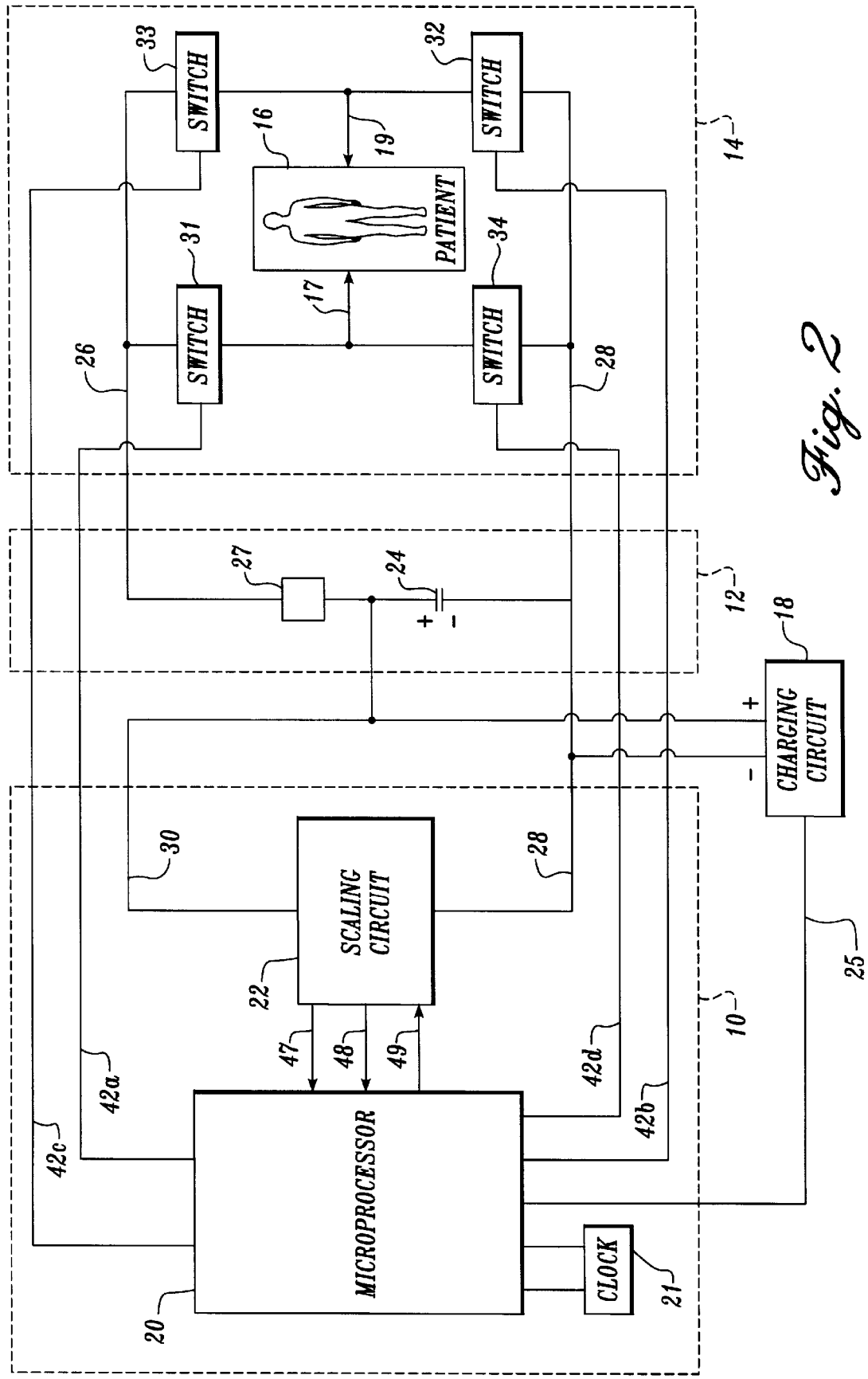
FIG. 2 is a block diagram of the external defibrillator of FIG. 1 depicting the construction of the output circuit and the connection of the output circuit to a scaling circuit.

The components of the defibrillator 8 are depicted in greater detail in FIG. 2. A microprocessor 20, scaling circuit 22, and charging circuit 18 are used to charge an energy storage capacitor 24 to a desired voltage. To control the charging, the microprocessor 20 is connected to the scaling circuit 22 by a pair of measurement lines 47 and 48, and by a control line 49. The microprocessor is also connected to the charging circuit 18 by a control line 25. The scaling circuit 22 and charging circuit 18 are connected to the energy storage capacitor 24 by a bridge line 28, which connects to the negative lead of the capacitor, and by a line 30, which connects to the positive lead of the capacitor. A clock 21 is also connected to the microprocessor 20.

Figure 4:
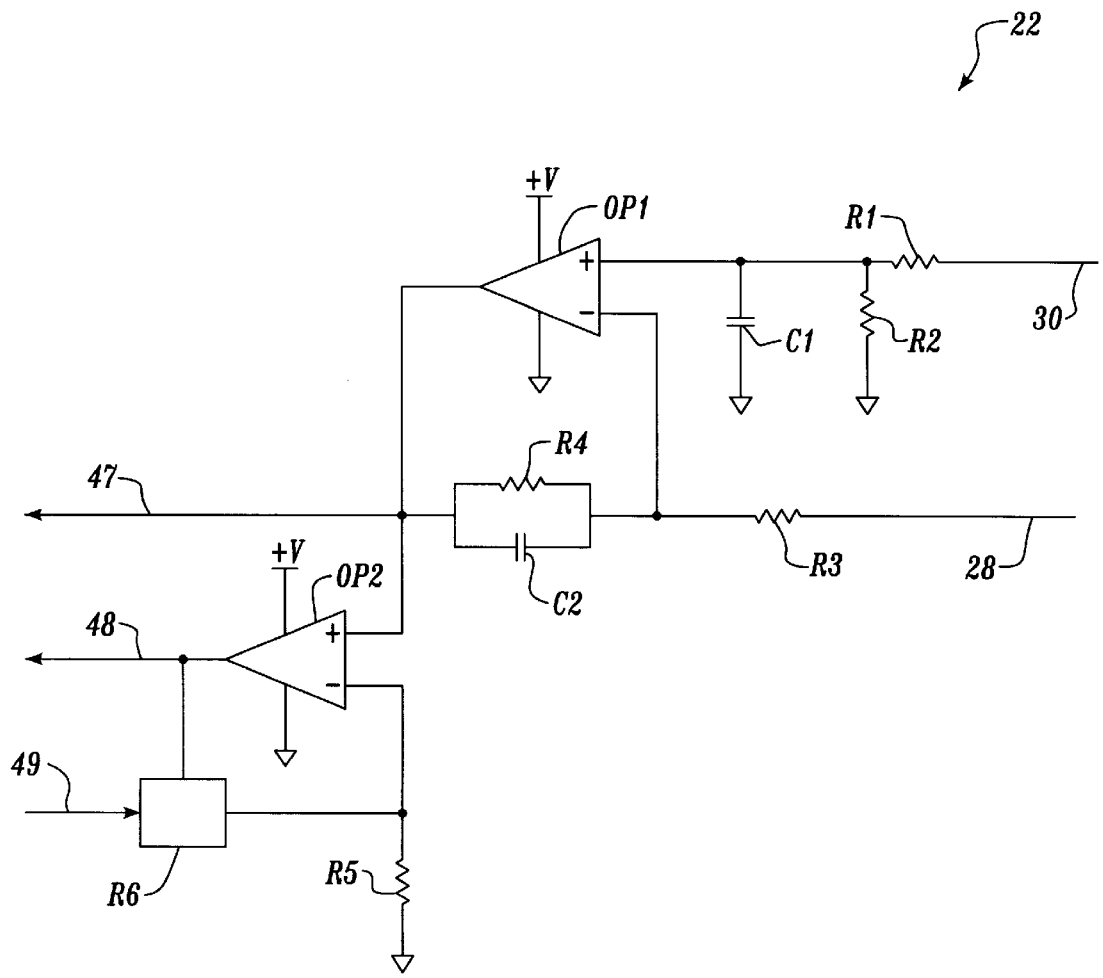
FIG. 4 is a schematic diagram of an actual embodiment of the scaling circuit of FIG. 2.

The scaling circuit 22 is used to monitor the voltage across the energy storage capacitor 24. FIG. 4 is a circuit diagram of an actual embodiment of the scaling circuit 22. The scaling circuit 22 steps down the voltage level across the energy storage capacitor 24 to a range that can be measured by the microprocessor 20 on measurement lines 47 and 48.

The scaling circuit 22 includes two operational amplifiers OP1 and OP2. A resistor R1 is connected between line 30 and the non-inverting input of operational amplifier OP1, and a resistor R2 and a capacitor C1 are connected in parallel between the non-inverting input of operational amplifier OP1 and ground. A resistor R3 is connected between the inverting input of operational amplifier OP1 and bridge line 28. A resistor R4 and a capacitor C2 are connected in parallel between the inverting input of operational amplifier OP1 and the output of operational amplifier OP1. The output of operational amplifier OP1 is connected to the non-inverting input of operational amplifier OP2 and to measurement line 47.

The DC voltage level of the energy storage capacitor 24 is stepped down for application to the operational amplifier OP1. The ratio of resistors R1 and R3 to resistors R2 and R4 is generally very high so as to significantly step down the voltage at this stage. The values of resistors R1 and R3 are also typically very high, so as to limit the current drain from the capacitor 24. The capacitors C1 and C2 are provided to filter out high-frequency voltage spikes. In an actual embodiment of the scaling circuit 22, the scaling circuit will step down a voltage of 2200V across the energy storage capacitor 24 to less than 5V on measurement line 47. The microprocessor 20 is provided with a 5V analog-to-digital converter to measure the voltage on the measurement line 47 and monitor the voltage across the energy storage capacitor 24.

If the energy storage capacitor 24 was always charged to 2200V, the scaling circuit described thus far would be adequate. In the preferred embodiment, however, the energy storage capacitor 24 can be charged to a range of voltage levels with the selected level depending on the patient and other parameters. The range to which the energy storage capacitor 24 may be charged in the preferred embodiment is from 100V to 2200V. To detect small percentage changes in the selected voltage level of the energy storage capacitor 24, the scaling circuit is therefore adjustable to account for different voltage ranges.

To account for the range of the input voltages into the scaling circuit 22, the non-inverting input of operational amplifier OP2 is connected to the output of operational amplifier OP1. A resistor R5 is connected between the inverting input of operational amplifier OP2 and ground. A digital variable gain pot R6 is connected between the inverting input of operational amplifier OP2 and the output of operational amplifier OP2. The digital variable gain pot R6 is controlled by a signal received on the control line 49 connected to the microprocessor 20. The output of operational amplifier OP2 is connected to measurement line 48. The gain provided by operational amplifier OP2 is adjustable by varying the setting of the digital variable gain pot R6.

The gain of the operational amplifier OP2 is set by the microprocessor 20. A measurement is initially made of the voltage on measurement line 47 which, as described above, in the actual embodiment ranges from 0 to approximately 5V. Based on the measured voltage, the gain of operational amplifier OP2 is adjusted to make the voltage on measurement line 48 close to 5V. Adjusting the output to nearly 5V allows the full range of precision of the 5V analog-to-digital converter in the microprocessor to be used. The microprocessor 20 uses the known gain of amplifiers OP1 and OP2 in conjunction with the output voltage provided on measurement line 48 to measure the energy storage capacitor 24 voltage level. As will be described in more detail below, changes in the energy storage capacitor voltage level are used to verify the integrity of the output circuit 14.

Returning to FIG. 2, the output circuit 14 allows the controlled transfer of energy from the energy storage capacitor 24 to the patient 16. The output circuit 14 includes four switches 31, 32, 33, and 34, each switch forming one leg of the H-bridge. Switches 31 and 33 are coupled through a protective component 27 to the positive lead of the energy storage capacitor 24 by bridge line 26. The protective component 27 has both inductive and resistive properties to limit the current and voltage changes from the energy storage capacitor 24. Switches 32 and 34 are coupled to the negative lead of the energy storage capacitor 24 by bridge line 28. The center cross line of the H-bridge includes the patient 16, which is connected to the left side of the bridge by an apex line 17, and to the right side of the bridge by a sternum line 19. Although omitted for clarity in FIG. 2, the apex line 17 and the sternum line 19 are connected to the electrodes 15a and 15b by the patient isolation relay 35. The microprocessor 20 is connected to the switches 31, 32, 33, and 34 by control lines 42a, 42b, 42c, and 42d, respectively, and to the patient isolation relay 35 by control line 36, allowing the switches and relay to be opened and closed under microprocessor control. Control lines 42a, 42b, 42c, and 42d are part of the control bus 42.

Figure 3:
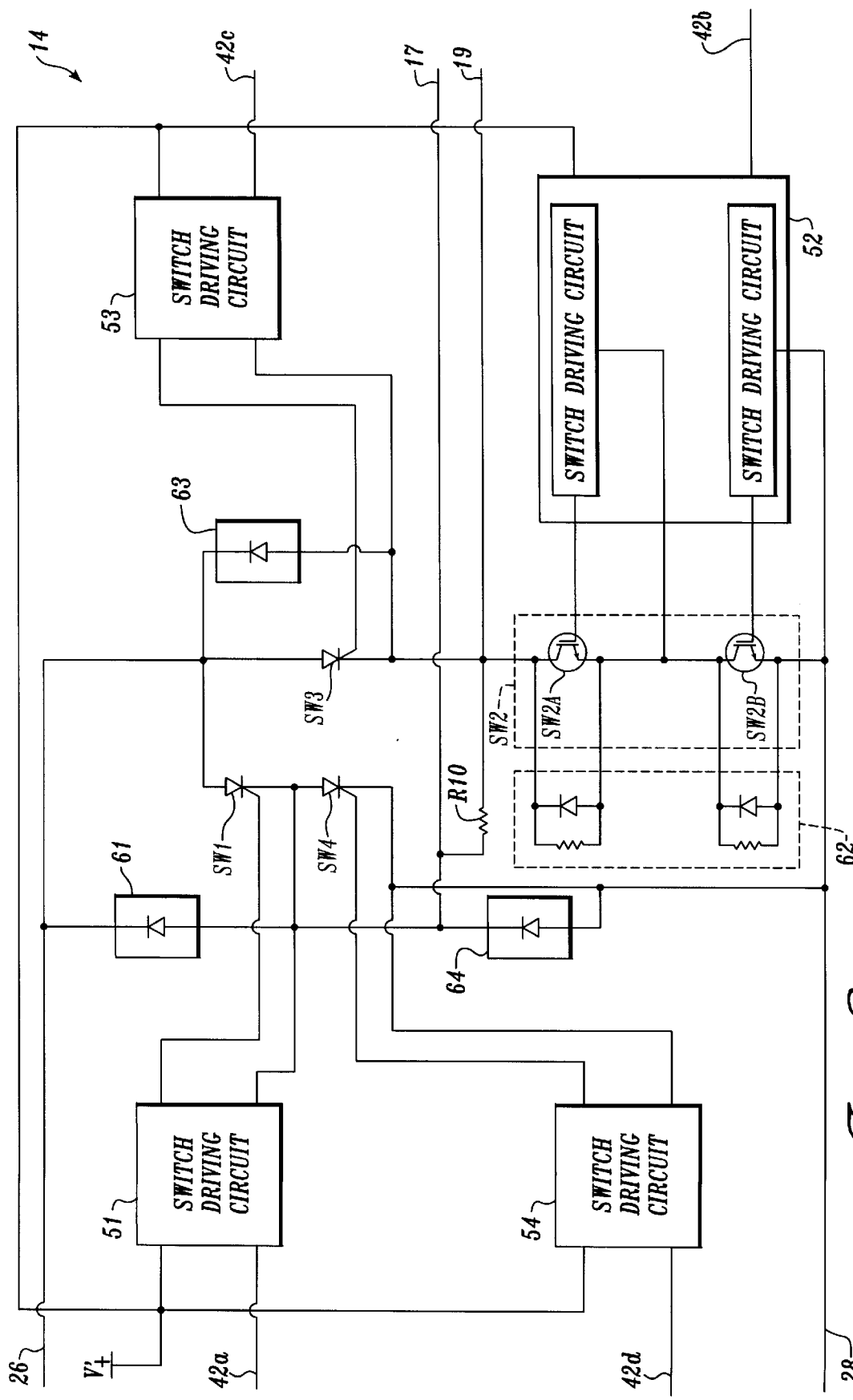
FIG. 3 is a schematic diagram of an actual embodiment of the output circuit of FIG. 2.

An actual embodiment of the output circuit 14 is shown in FIG. 3. The circuit diagram of FIG. 3 is described briefly below, and is also described in detail in a copending application entitled "H-Bridge Circuit for Generating a High-Energy Biphasic Waveform in an External Defibrillator," (attorney docket no. PHYS19377), filed concurrently herewith and hereby incorporated by reference. As shown in FIG. 3, four output switches SW1 to SW4 allow the transfer of energy from the energy storage capacitor on lines 26 and 28. Switches SW1, SW3, and SW4 are semiconductor switches, preferably silicon controlled rectifiers (SCRs). Switch SW2 is a series combination of switches SW2A and SW2B, which are both insulated gate bipolar transistors (IGBTs). The four output switches SW1 to SW4 can be switched from an off (non-conducting) to an on (conducting) condition. Control lines 42a, 42b, 42c, and 42d are connected to switch driving circuits 51, 52, 53, and 54, which are connected to switches SW1 to SW4, respectively. Switch driving circuit 52 contains two identical switch driving circuits, each circuit corresponding to one of the IGBTs.

The switch driving circuits 51, 53 and 54 switch the respective SCR switches on or off according to signals on control lines 42a, 42c, and 42d. Switches SW1, SW3, and SW4 remain conducting as long as the signal on the corresponding control line is present. Each switch SW1 to SW4 is also connected to a switch protection circuit 61, 62, 63, and 64, respectively. Switch driving circuit 52 switches the IGBT switches on or off according to a signal on control line 42b. As long as the signal on control line 42b is present, switch SW2 will remain conducting. Switch protection circuit 62 contains two identical switch protection circuits, each protection circuit corresponding to one of the IGBTs. Switch protection circuits 61, 62, 63, and 64 protect the switches SW1 to SW4 from being damaged by reverse voltages, and from conducting prematurely.

In the preferred embodiment, the defibrillator 8 provides a biphasic defibrillation pulse to the patient in the following manner. With reference to FIG. 3, once the energy storage capacitor 24 is charged to a selected energy level and the patient isolation relay 35 is closed, the switches SW1 and SW2 are switched on so as to provide a path from the energy storage capacitor to apex line 17 and sternum line 19, respectively, for the application of a first phase of a defibrillation pulse to the patient. The stored energy travels from the positive terminal of the capacitor 24 on line 26, through switch SW1, across apex line 17, across the patient 16, back across sternum line 19, and through switch SW2 to the negative terminal of the capacitor 24 on line 28. The first phase of the biphasic pulse therefore applies a positive pulse from the apex to the sternum of the patient.

Before the energy storage capacitor 24 is completely discharged, switch SW2 is biased off in preparation for applying the second phase of the biphasic pulse. Once switch SW2 is biased off, switch SW1 will also become non-conducting because the voltage across the SCR falls to zero.

After the end of the first phase of the biphasic defibrillation pulse, the switches SW3 and SW4 are switched on to start the second phase of the biphasic pulse. Switches SW3 and SW4 provide a path to apply a negative defibrillation pulse to the patient. With reference to FIG. 3, the energy travels from the positive terminal of the capacitor 24 on line 26, through switch SW3, across sternum line 19, through the patient 16, back across apex line 17, and out through switch SW4 to the negative terminal of the capacitor 24 on line 28. The polarity of the second phase of the defibrillation pulse is therefore opposite in polarity to the first phase of the pulse. The end of the second phase of the biphasic pulse is truncated by switching on switch SW1 to provide a shorted path for the remainder of the capacitor energy through switches SW1 and SW4. After the second phase is truncated, all four of the switches SW1 to SW4 are switched off. The patient isolation relay 35 is also opened to allow the energy storage capacitor 24 to be recharged in preparation for providing another defibrillation pulse.

Figure 5A:
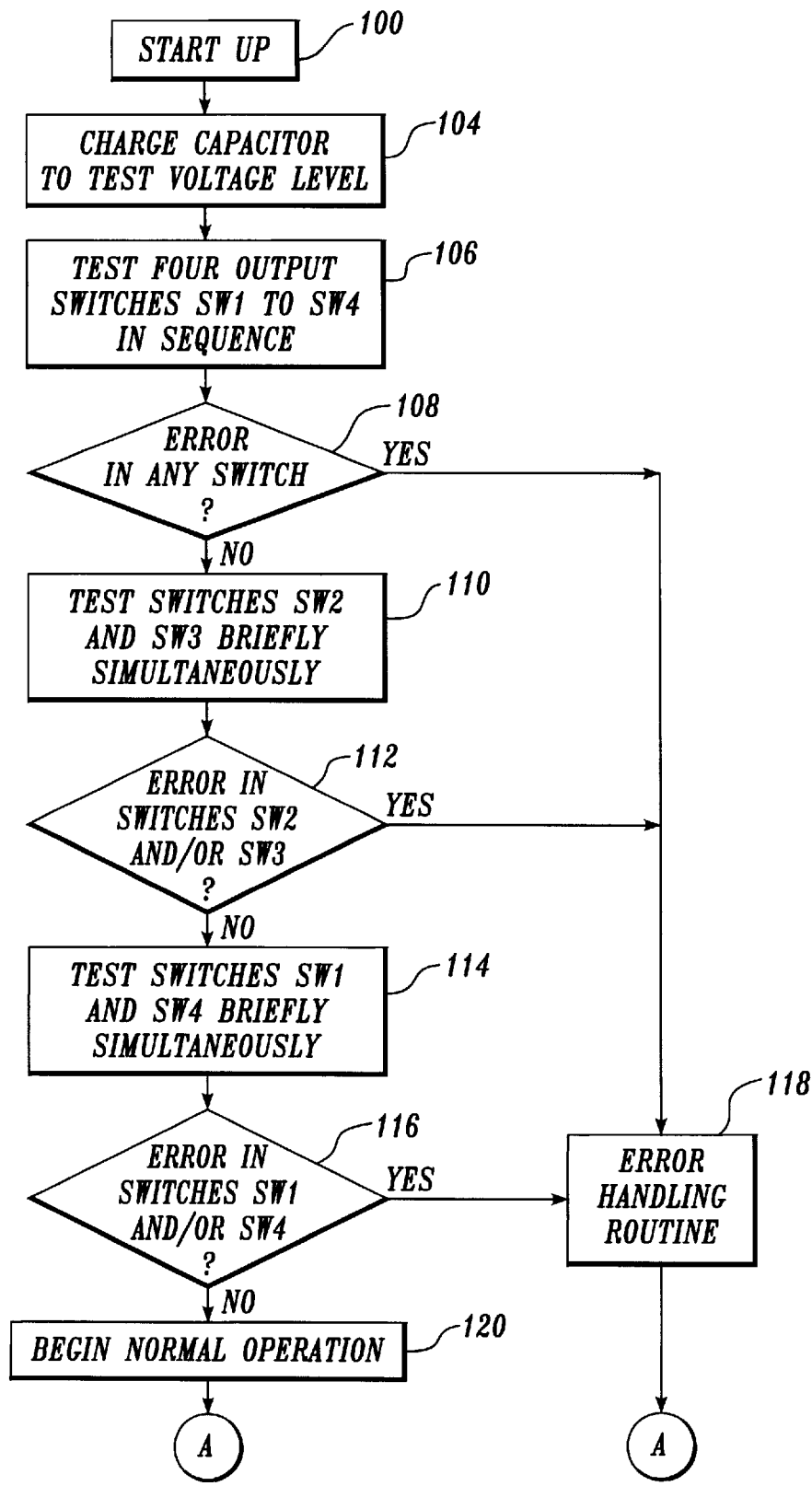
FIGS. 5A–5B are flow charts of an exemplary routine for testing the output circuit prior to and during the delivery of a defibrillation pulse to a patient.

The integrity of the output circuit 14 is verified prior to and during the delivery of a defibrillation pulse. A preferred method of verifying the integrity of the output circuit 14 is illustrated in the flow charts of FIGS. 5A–5B. FIG. 5A depicts a start-up verification test performed after the defibrillator is turned on and prior to delivery of a defibrillation pulse. After turning on the defibrillator at a block 100, the energy storage capacitor is charged to a test voltage at a block 104. The test voltage to which the energy storage capacitor is charged may be less than the maximum allowed voltage of the capacitor if energy conservation during the start-up test is desired. A lower voltage requires less charging time, and therefore allows the total start-up test time of the output circuit to be shortened. The test voltage should be high enough, however, to allow a reasonable test of the integrity of the output switches SW1 to SW4, as set forth below. During the entirety of the start-up verification test of the output circuit, it will be appreciated that the patient isolation relay 35 is opened to prevent any current from flowing to a patient.

After charging the energy storage capacitor, at a block 106 a sequential test is made of the four output switches SW1 to SW4. The output switches are initially tested by switching the switches off. After placing each of the switches in the non-conducting state, each switch is individually switched on and then off again in sequence. That is, the first switch SW1 is switched on and then off, followed by the remaining switches in turn. As the switches are being switched on and off, the voltage level across the energy storage capacitor is monitored. No change in the voltage level across the energy storage capacitor 24 should occur during the tests, because switching on a single switch does not provide a conductive path through the output circuit 14 that would allow the energy stored in the energy storage capacitor to discharge. If any change in the voltage level across the capacitor during the sequential switching on and off of switches SW1 to SW4 is detected, an error is indicated. At a block 108, a test is made to determine whether there were errors detected in any of the switches SW1 to SW4. If any errors were detected in the switches, at a block 118 an error handling routine is called. The error handling routine will be described in additional detail below. If no errors were detected in the switches, the start-up verification test proceeds to a block 110.

At block 110 the switches SW2 and SW3 are tested simultaneously for a brief interval. The two switches are tested by simultaneously switching on both switch SW2 and SW3. The switches are turned off by biasing switch SW2 off, which causes switch SW3 to become non-conducting since it is an SCR. When switches SW2 and SW3 are simultaneously conducting, a drop in the voltage across the energy storage capacitor should be detected due to the shorted path that is provided through the output circuit 14. If a voltage drop is not detected when switches SW2 and SW3 are supposed to be simultaneously conducting, then an error is indicated. At a block 112, a test is made to determine whether an error was detected in the combination of switches SW2 and SW3. If an error was detected, the start-up verification test continues to the error handling routine at block 118. If no error was detected in switches SW2 and SW3, the start-up test continues to a block 114.

At block 114, a test is made of switches SW1 and SW4. Switches SW1 and SW4 are tested by simultaneously switching the switches on. Switching on switches SW1 and SW4 causes a conductive path to be created from the energy storage capacitor 24 through the output circuit 14. A voltage drop across the energy storage capacitor should therefore be detected. If a voltage drop is not detected when switches SW1 and SW4 are simultaneously switched on, then an error is indicated. At block 116, a test is made to determine whether an error was detected in the combination of switches SW1 and SW4. If an error was detected, the start-up test continues to the error handling routine at block 118. If no error was detected in switches SW1 and SW4, the start-up test continues to block 120 where the defibrillator enters normal operation.

It will be appreciated that in the embodiment of the output circuit 14 shown in FIG. 3, the set of switches SW2 and SW3 must be tested before the set of switches SW1 and SW4. If switches SW1 and SW4 had been tested first, it would have been impossible to switch the switches SW1 and SW4 off while current was flowing through them because they are both SCR devices. Testing switches SW1 and SW4 first would therefore have drained all the test energy from the energy storage capacitor 24. Because switch SW2 is an IGBT pair that can be made non-conducting, the combination of switches SW2 and SW3 can be switched off. Testing the switches in the correct order therefore allows the energy storage capacitor to be charged a single time in order to test all four switches. It will be appreciated, however, that a different switch testing order could be used if the capacitor were recharged or if different switches were used in the output circuit.

The start-up verification test is performed immediately after turning the defibrillator on because it requires extra time and energy to charge and then dissipate the energy in the energy storage capacitor. The amount of time and energy that the start-up tests takes can be varied by changing the voltage level to which the energy storage capacitor is charged. Using a lower voltage level reduces the charge time of the capacitor. In an alternate embodiment, a "skip start-up test" button or command may also be incorporated in the defibrillator to allow a user to bypass the start-up verification test as the defibrillator is powered on.

In addition to being performed when a user powers on the defibrillator, in an alternate embodiment the start-up verification test may also be performed periodically by the microprocessor 20 while the defibrillator is not in use. For example, at a certain time each night as shown by clock 21, the microprocessor 20 could automatically and without user intervention power on the defibrillator, perform tests to verify the integrity of the output circuit, and, as described below with respect to the error handling routine, provide a warning signal to a user if a failure has occurred.

Figure 5B:
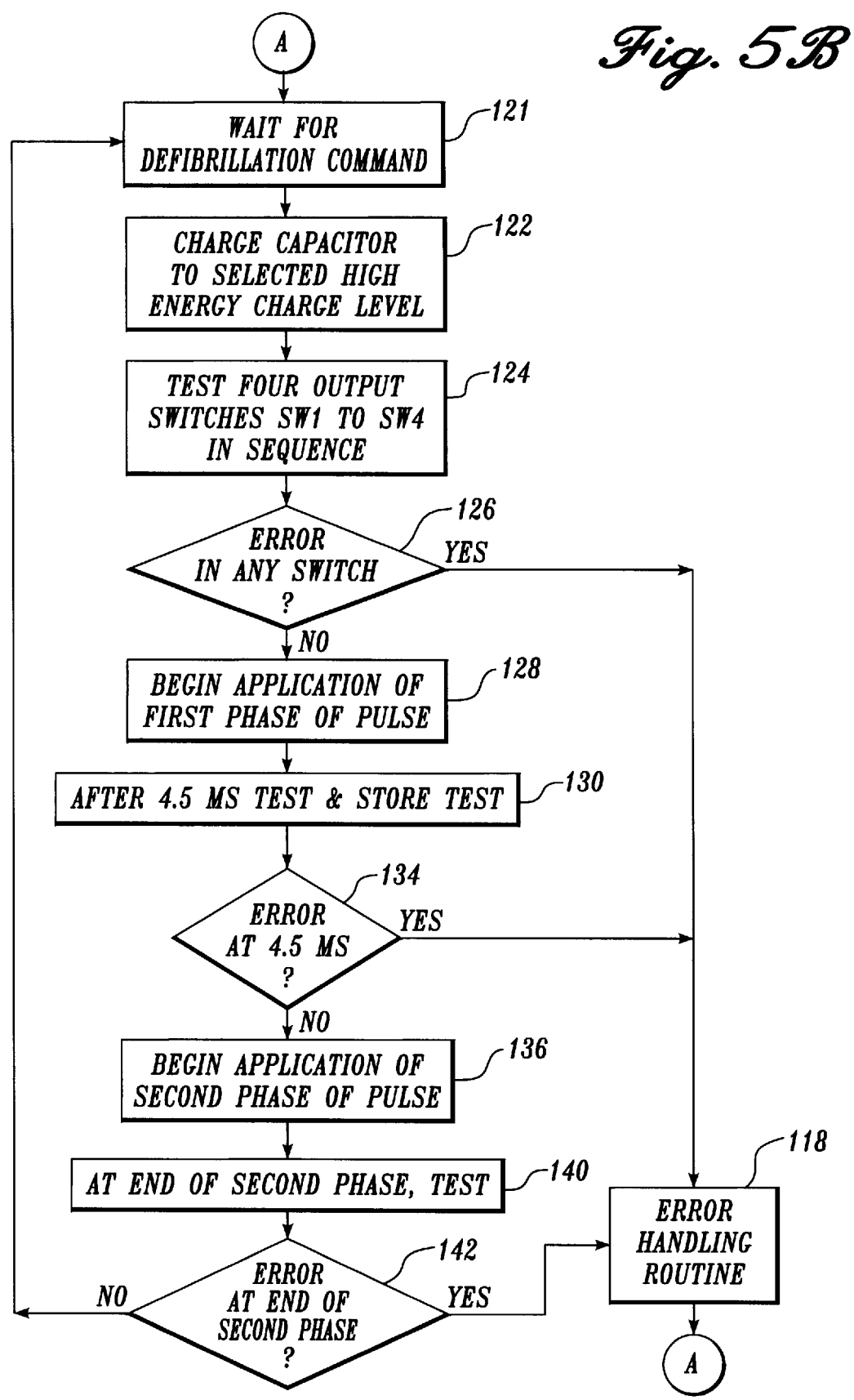

FIG. 5B depicts the verification tests performed immediately prior to, and during the delivery of, a defibrillation pulse. After entering the normal mode of operation, at a decision block 121 the defibrillator waits to receive a command indicating that a defibrillation pulse is to be applied to a patient. If implemented in an automatic defibrillator, the command will be generated by the microprocessor after analysis of an electrocardiogram from the patient. Alternatively, in a manual defibrillator, the command to charge the energy storage capacitor for application of a defibrillation pulse may come from trained medical personnel using the device.

If a command is received indicating that the defibrillator should prepare to apply a defibrillation pulse to a patient, the verification test proceeds to a block 122. At block 122 the energy storage capacitor 24 is charged to a selected voltage. Several factors determine the charge level of the capacitor, including the selected energy level that is to be delivered to the patient.

After charging the capacitor to the desired voltage, at a block 124 a test is made of the four output switches SW1 to SW4. The test is identical to the test performed at block 106. That is, each of the switches are individually switched on and then off. While the switches are switched on and off, the voltage across the energy storage capacitor is monitored by the microprocessor. If all the switches are operational (i.e., none of the switches are stuck in a conducting state), the voltage across the energy storage capacitor should not change during the testing. The verification test performed at block 124 is capable of being performed prior to delivery of the defibrillation pulse because the test can be performed quickly and with no energy loss from the energy storage capacitor if no faults occur. If a faulty switch is identified that is stuck in a conducting state prior to delivery of the defibrillation pulse, the verification test can discover the error before the defibrillator attempts to deliver the defibrillation pulse to the patient.

After testing each of the switches, at a block 126 a test is made to determine if there were any errors detected in any of the switches. If any errors were detected, then at block 118 the error handling routine is called. If no errors were detected in the switches, the defibrillator may deliver the defibrillation pulse to the patient. The patient isolation relay 35 is closed prior to the delivery of the defibrillation pulse.

At a block 128, switches SW1 and SW2 are switched on to start the application of the first phase of the defibrillation pulse. As the first phase of the pulse is being delivered to the patient, a clock is started. After a predetermined time from the start of the first phase, preferably 4.5 milliseconds, the microprocessor measures the voltage on the energy storage capacitor at a block 130. After 4.5 milliseconds, the voltage level of the capacitor should have dropped to within a certain range that is defined based on the known range of patient impedances. If the measured voltage level across the energy storage capacitor is not within the expected range after 4.5 milliseconds, then a failure is present in either the output circuit or the connection to the patient. At a decision block 134, a test is made to determine if a failure was detected at 4.5 milliseconds. If a failure was detected, an error handling routine is called at block 118. If a failure was not indicated during delivery of the first phase, then the second phase of the biphasic defibrillation pulse may be applied to the patient. Prior to starting the second phase, switch SW2 is switched off to truncate the application of the first phase.

At a block 136, switches SW3 and SW4 are switched on to provide a conductive path from the energy storage capacitor to the patient and begin the application of the negative second phase of the defibrillation pulse. At a block 140, a measurement is made of the voltage across the capacitor at the end of the second phase. The measured voltage at the end of the second phase should fall within a certain range based on the expected patient impedances. If the measured voltage falls outside the expected range, a failure of the output circuit or the connection to the patient is indicated.

At a decision block 142, a test is made to determine if a failure was indicated at the end of the second phase. If a failure was indicated, the verification test proceeds to the error handling routine at block 118. If no failure was indicated, the verification test returns to decision block 121 to wait to receive another command to charge the energy storage capacitor for delivery of an additional defibrillation pulse. After the end of the second phase, the patient isolation relay 35 is opened to isolate the patient from the defibrillator.

It will be appreciated that while the 4.5 millisecond test performed at block 130 was only performed during the first phase of the defibrillation pulse, a similar test could have been performed 4.5 milliseconds after the start of the second phase. Similarly, while the test of the ending voltage performed at block 140 was only performed at the end of the second phase, a similar test could have been performed at the end of the first phase.

The testing method disclosed herein is advantageous in that it allows the integrity of the output circuit and connection to the patient to be checked both before and during the application of the defibrillation pulse. Many prior defibrillators were unable to perform such testing due to the type of output switch and the EMI noise generated by the application of a defibrillation pulse. If any error is detected before or during delivery of the defibrillation pulse, an error handling routine may be called to analyze and compensate for the indicated failure.

Figure 6A:
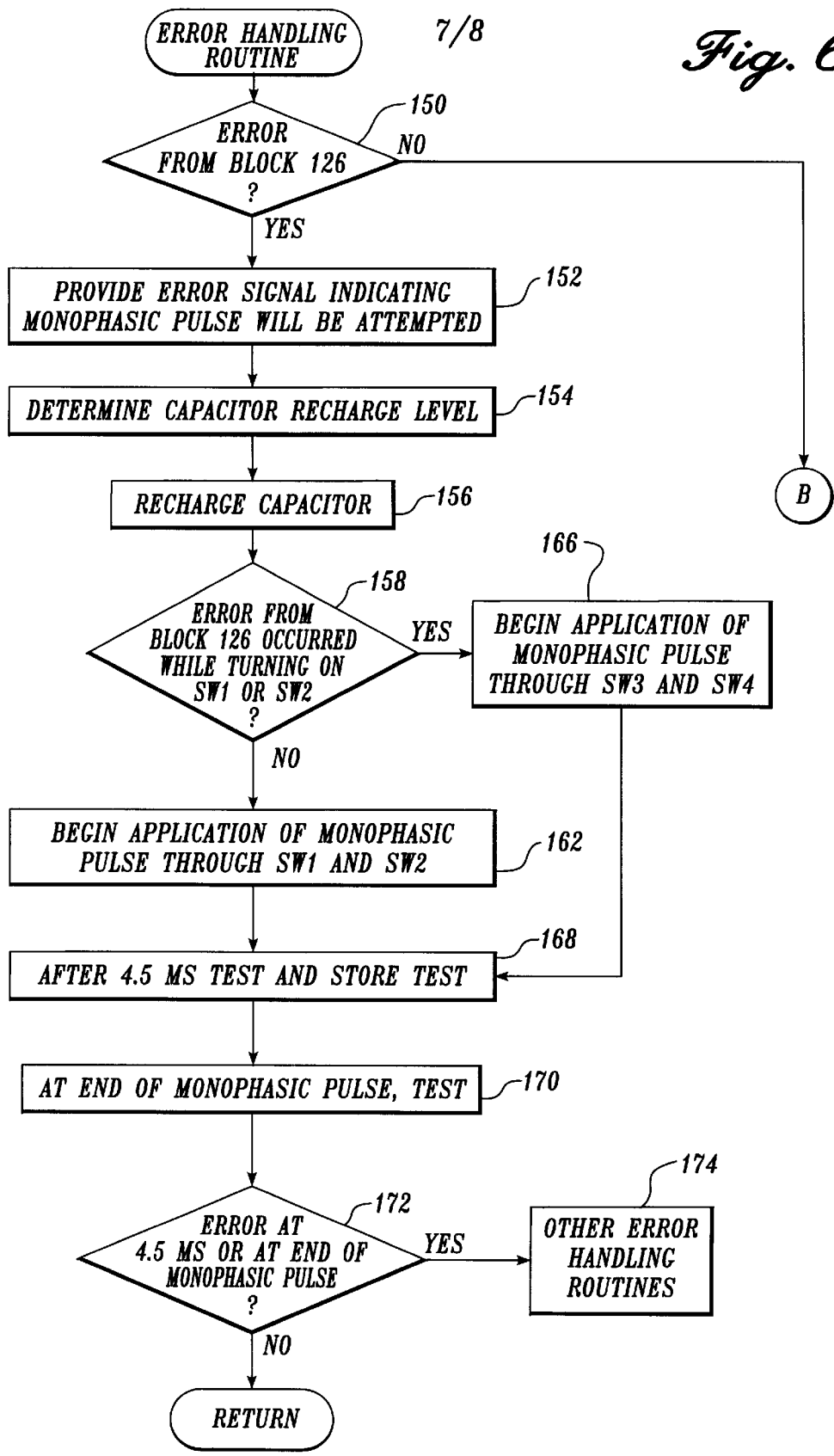
FIGS. 6A–6B are flow charts of an exemplary error handling routine for analyzing and compensating for particular errors should an error be detected while testing the output circuit.
Figure 6B:
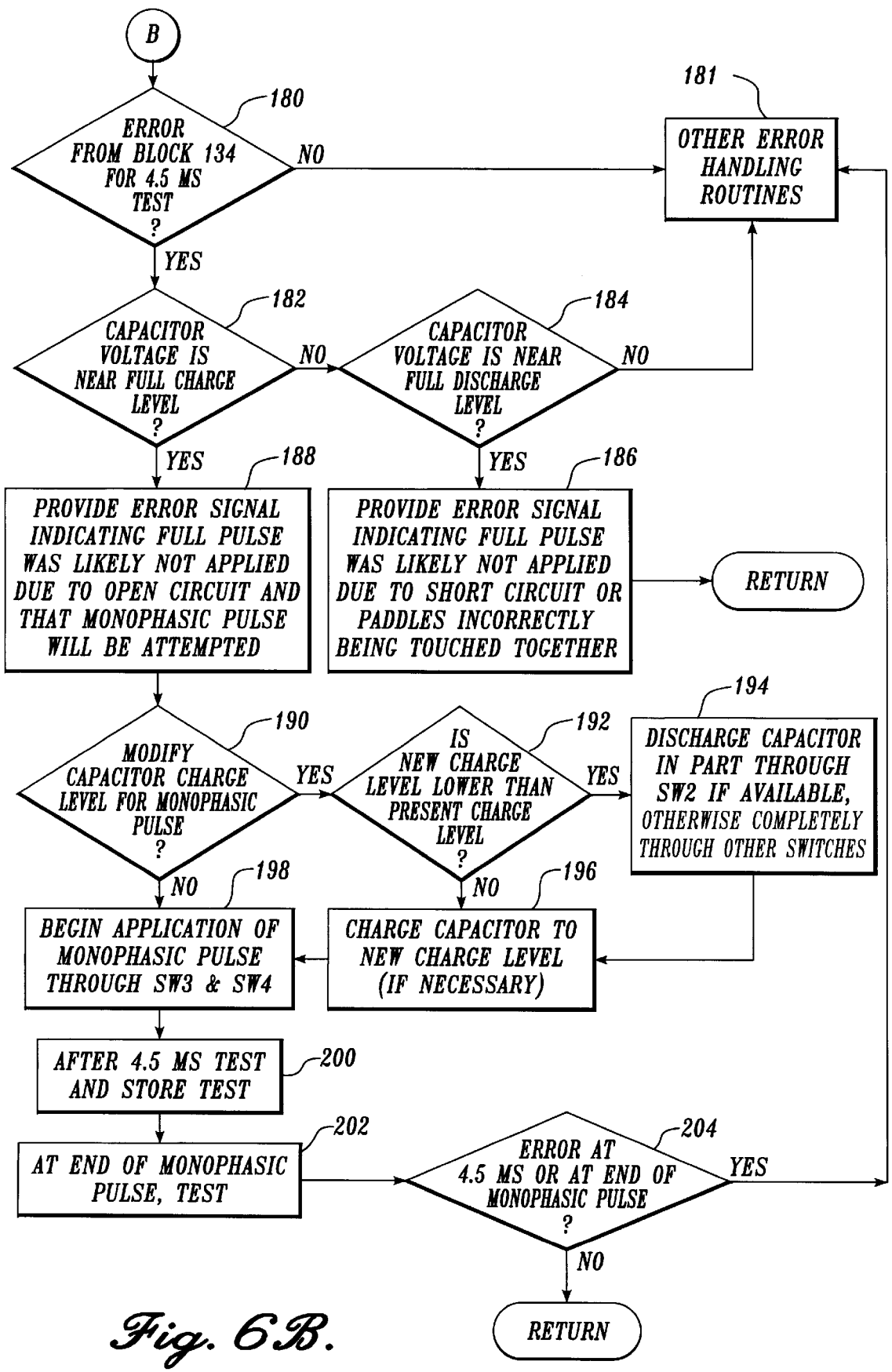

When an error is indicated before or during delivery of a defibrillation pulse, the error handling routine is called at block 118. The error handling routine may perform several types of analyses to further determine the cause of the error. If possible, the error handling routine may also compensate for the error by applying a monophasic, rather than a biphasic, pulse to the patient. FIGS. 6A and 6B are flow charts of a representative error handling routine.

If one of the switches in the output circuit is stuck in the conducting state, the defibrillator may compensate for the stuck switch by using the available conducting switching path to deliver a monophasic, rather than a biphasic, pulse. FIG. 6A illustrates the application of a monophasic pulse if the failure of a switch is detected prior to a defibrillation pulse being applied. At a block 150, a test is made to determine if the error handling routine was entered from block 126. If the error handling routine was not entered from block 126, the routine proceeds to a block 180. If the error handling routine was entered from block 126, the routine proceeds to a block 152.

At block 152, an error signal is provided to the user to indicate that an error has occurred and that a monophasic pulse will be attempted. The error signal may be an audible, visual, and/or logged alarm. At a block 154, a determination is made as to whether the current charge level of the energy storage capacitor is sufficient to generate a desired monophasic pulse. It will be appreciated that the size of a desired monophasic pulse may be varied depending on the impedance of the patient, the number of shocks previously applied to the patient, and other factors. To change the duration and magnitude of the monophasic pulse, the energy storage capacitor 24 charge level is modified. If the monophasic pulse is to have a higher current or longer duration than the pulse that would be delivered based on the current charge level on the capacitor, the energy storage capacitor is charged to a higher voltage. Conversely, if the monophasic pulse is to have a lower current or shorter duration, the voltage on the capacitor is reduced. To reduce the voltage, the capacitor 24 can be discharged in part through a shorted path provided by closing both output switches on one side of the H-bridge output circuit 14. At a block 156, the energy storage capacitor 24 is charged to the selected level. The patient isolation relay 35 is also closed to prepare for the application of the monophasic pulse.

At a block 158, a test is made to determine the specific output switch that is stuck in a conducting state. If during the tests at blocks 106 or 124 a shorted conducting path is formed so that the voltage on the capacitor 24 changes rapidly when only switch SW1 is switched on, then it is logical to infer that either switch SW4 is stuck in a conducting state or else that there is a short somewhere in the system. This logic follows because of the three remaining switches when switch SW1 is supposed to be conducting, only switch SW4 being conductive should cause a shorted conductive path to be formed. Similarly, a rapid voltage change when only switch SW2 is switched on may indicate that switch SW3 is stuck in a conducting state, and vice versa. An error detected while switch SW1 or SW2 is switched on may therefore indicate that switch SW4 or SW3, respectively, is stuck in a conducting state and vice versa. If the error was indicated in switches SW1 or SW2, the error routine proceeds to a block 162 where it begins the application of the monophasic pulse through switches SW1 and SW2. Switches SW1 and SW2 are required to be used in this circumstance because if one of them is stuck in a conducting state, then switches SW1 and SW2 provide the only effective defibrillation path. Similarly, if the error was indicated in switches SW3 or SW4, the routine proceeds to a block 166 where it begins the application of the monophasic pulse through switches SW3 and SW4.

From either block 162 or block 166, the routine proceeds to a block 168, where a measurement is made of the voltage across the energy storage capacitor at a predetermined time after the start of the monophasic pulse. Preferably, the voltage measurement is made at 4.5 milliseconds. The rate of decay of the monophasic pulse is dependent on a known range of patient impedances. After 4.5 milliseconds, the measured voltage across the energy storage capacitor should therefore fall within an expected range. If the voltage across the energy storage capacitor falls outside the expected range, a failure of the output circuit or of the connection to the patient is indicated.

At a block 170, a measurement is made of the voltage across the capacitor at the end of the monophasic pulse. The measured voltage at the end of the monophasic pulse should fall within a certain range based on the expected patient impedances. If the measured voltage falls outside the range, a failure of the output circuit or of the connection to the patient is indicated.

At a decision block 172, a test is made to determine if a failure was indicated at either 4.5 milliseconds or at the end of the monophasic pulse. If a failure was indicated, the routine proceeds to other error handling routines at block 174. If no failure was indicated, the routine returns to block 121 to wait for another defibrillation command, under the theory that the original error condition identified in block 126 may have been merely a transient condition. In an alternate embodiment, rather than proceeding back to block 121, the routine may proceed to a block which again applies a monophasic pulse when the next defibrillation command is given.

FIG. 6B illustrates the analysis and attempted compensation that occurs if an error is detected during the application of a biphasic defibrillation pulse. At a block 180, a test is made to determine if the error handling routine was entered from block 134 due to an error that was detected 4.5 milliseconds after the start of the first phase of the defibrillation pulse. If the routine was not called from block 134, the routine proceeds to a block 181 where other error handling routines are called. If the routine was initially called from block 134, the routine proceeds to a block 182.

At block 182 a test is made to determine if the energy storage capacitor voltage that was measured at block 130 is above the expected range and near the fully charged level. If the voltage is not near the fully charged level, the routine proceeds to a block 184. At block 184 a test is made to determine if the energy storage capacitor voltage that was measured at block 130 is near the fully discharged level. If the voltage is not near the fully discharged level, the routine proceeds to a block 181 where other error handling routines are called. If the voltage is near the fully discharged level, the routine proceeds to a block 186 where an error signal is provided to the user of the defibrillator indicating that the full defibrillation pulse was likely not applied to the patient. After block 186 the routine returns to block 121 to wait for another defibrillation command, under the theory that the original error identified in block 134 may have been a transient problem. The error signal provided at block 186 illustrates one aspect of the importance of the test performed during the application of a defibrillation pulse. Tests made after the pulse is over only indicate that the energy has been discharged, and do not indicate if the energy went through the patient or through a short circuit. Tests made during the defibrillation pulse, however, provide an accurate indication that the defibrillation pulse was applied to the patient.

Returning to block 182, if the voltage across the energy storage capacitor is near the fully charged level, the routine proceeds to a block 188. At block 188 an error signal is provided to the user indicating that the capacitor voltage is still near the full charge level and that a monophasic pulse will be attempted. A full charge on the capacitor likely indicates a switch failure or an open circuit within the defibrillator. At a block 190, a test is made to determine if the charge level of the capacitor should be changed before the application of the monophasic pulse. As was described above, changing the charge level alters the current and duration of the monophasic pulse. The desired current and duration may be selected based on various parameters, including the impedance of the patient and whether the patient has been shocked before. If the charge level does not need modification, the routine proceeds to a block 198. If the charge level is to be modified, the routine proceeds to a block 192.

At block 192 a test is made to determine if the desired charge level is higher or lower than the present charge level. If the desired charge level is higher, the routine proceeds to a block 196. If the desired charge level is lower, the routine proceeds to a block 194 where an attempt is made to lower the charge level by switching on switches SW2 and SW3 to provide a shorted path across the capacitor. An attempt is made to use switches SW2 and SW3 first because, as described above, switch SW2 may be biased off before all of the energy of the storage capacitor is discharged. If switch SW2 is not available at block 194, switches SW1 and SW4 are switched on to discharge all the energy of the capacitor. After block 194 the routine proceeds to block 196.

At block 196, if necessary, the energy storage capacitor is charged to a new level. The routine then proceeds to block 198, where the monophasic pulse is applied by turning on switches SW3 and SW4. Switches SW1 and SW2 are not used for the application of the monophasic pulse because the routine was called when an open circuit error was indicated while attempting to provide a pulse through switches SW1 and SW2.

After 4.5 milliseconds of the monophasic pulse have elapsed, a measurement is made of the voltage across the energy storage capacitor at a block 200. At a block 202 a measurement of the voltage across the storage capacitor is made at the end of the monophasic pulse. If the voltage is outside the expected range for either test, a failure of the output circuit or of the connection to the patient is indicated.

At a decision block 204 a test is made to determine if a failure was indicated at either 4.5 milliseconds or at the end of the monophasic pulse. If a failure was indicated, the routine proceeds to other error handling routines at block 181. If no failure was indicated, the routine returns to block 121 to wait for another defibrillation command, under the theory that the original error condition in block 134 may have been cleared. In an alternate embodiment, rather than proceeding back to block 121, a monophasic pulse may be automatically applied when the next defibrillation command is given.

Providing a monophasic pulse if a portion of the output circuit should fail offers a distinct advantage over prior monophasic, including Edmark pulse, defibrillators. Generally, in prior monophasic defibrillators, there was only one active switching path, and if part of that path failed, the defibrillator became inoperable. In the present invention, the existence of two conductive paths through the H-bridge output circuit 14 provides a "backup" path that can be used for providing a monophasic pulse in the event that one of the paths fails.

The analysis depicted in FIGS. 6A and 6B is merely representative of some of the diagnostic tests that may be performed on the output circuit to analyze an error condition. Those skilled in the art will recognize that other tests could also be envisioned. For example, another possible type of analysis that the error handling routine may perform is locating a specific output switch that is stuck in a non-conducting state. If during the tests in block 110 a shorted path is not formed such that the voltage on the capacitor 24 does not quickly change when switches SW2 and SW3 are supposed to be conducting, then it is logical to infer that either switch SW2 or SW3, or both, is stuck in a non-conducting state, or else that there is an open circuit in the system. Similarly, a lack of rapid voltage change when switches SW1 and SW4 are supposed to be conducting in block 114 may indicate that either switch SW1 or SW4, or both, is stuck in a non-conducting state. Given this information alone, it cannot be determined exactly which of the two switches being tested is stuck, because if either or both of the two switches are stuck in a non-conducting state, the voltage will not change. Once it is determined that either or both of the switches may be stuck in a non-conducting state, however, appropriate error messages and instructions can be provided to the user and additional tests can be performed to specifically locate the faulty switch. One response that the defibrillator may invoke when such an error occurs and the faulty switch is specifically located is to deliver a monophasic rather than a biphasic pulse, using the switching path that is available for such a pulse, possibly with higher current or longer duration.

Another type of analysis that the error handling routine may perform is determining the cause of erroneous voltage readings that are measured at blocks 130 and 140. A measured voltage level that is too high may indicate that there is too much impedance, i.e., that the paddles or electrodes are not being properly applied to the patient. No voltage drop at all may indicate that one of the switches SW1 to SW4 is stuck in a non-conducting state. A specific output switch being stuck in a non-conducting state can be pinpointed by this test combined with the tests at blocks 110 and 114. A measured voltage level that is too low may indicate that a switch is stuck in a conducting state or that the electrodes have been touched together.

While the preferred embodiment of the invention has been illustrated and described, it will be apparent that various changes can be made therein without departing from the spirit and scope of the invention. For example, while the preferred embodiment contemplates using the output circuit to generate a biphasic defibrillation pulse to a patient, the output circuit may also be used to generate a multiphasic defibrillation pulse with three or more phases.

It will also be appreciated that while the voltage across the energy storage capacitor was the measured parameter for the tests performed in FIGS. 5A to 5B, any parameter that is related to the energy flow from the capacitor to the patient may be used to estimate the impedance of the discharge. For example, the current of the discharge, the time of the discharge, or the voltage/current ratio could all be compared against expected ranges that are defined based on the known range of patient impedances. Any measured parameter that was not within the expected range could indicate a failure in the output circuit.

Moreover, while a microprocessor 20 is used in the preferred embodiment to control testing and analysis of the output circuit 14, it will be appreciated that other controllers could be used to perform the same task. For example, an ASIC or discrete logic could be used to govern the testing. It will also be appreciated that while a single energy storage capacitor 24 is depicted herein, other energy storage devices could be envisioned. For example, multiple capacitors could be coupled to store the desired amount of energy.

It will further be appreciated that while switches SW1, SW3 and SW4 are depicted as comprising only a single semiconductor device, multiple semiconductor devices could be coupled in series to perform the same switching function. The method described above to test each leg is equally applicable to legs having multiple switches. Also, the switch elements for switches SW1 to SW4 could be SCRs, IGBTs, MOSFETs, BJTs, MCTs, or any other high voltage semiconductors. Consequently, within the scope of the appended claims, it will be appreciated that the invention can be practiced otherwise than as specifically described herein.

The embodiments of the invention in which an exclusive property or privilege is claimed are defined as follows:

1. In an external defibrillator, a method of verifying the integrity of an output circuit prior to application of a multiphasic defibrillation pulse to a patient, the output circuit having a plurality of switches coupled to an energy storage capacitor in a configuration having four legs to allow the energy storage capacitor to be electrically coupled to the patient for application of the multiphasic defibrillation pulse, the method comprising the steps of:

(a) placing all of the plurality of switches associated with one of the four legs in the output circuit in a conducting state so that current may be conducted through the one leg prior to application of the multiphasic defibrillation pulse;

(b) placing at least one of the plurality of switches associated with each of the other three of the four legs in the output circuit in a non-conducting state so that current is not conducted through the other three legs;

(c) monitoring a parameter associated with the one leg to ensure that current does not flow through the one leg from the energy storage capacitor when placed in the conducting state; and (d) repeating steps (a)–(c) for the other three of the four legs in the output circuit.

2. The method of claim 1, wherein the parameter is a voltage across the energy storage capacitor.

3. The method of claim 1, further comprising the step of charging the energy storage capacitor to a testing voltage.

4. The method of claim 1, further comprising the step of providing a warning indication to a user of the external defibrillator if current flows through one leg.

5. In an external defibrillator, a method of verifying the integrity of an output circuit prior to application of a multiphasic defibrillation pulse to a patient, the output circuit having a plurality of switches coupled to an energy storage capacitor in a configuration having four legs to allow the energy storage capacitor to be electrically coupled to the patient for application of the multiphasic defibrillation pulse, the method comprising the steps of:

(a) placing all of the plurality of switches associated with one of the four legs in the output circuit in a conducting state so that current may be conducted through the one leg prior to application of the multiphasic defibrillation pulse;

(b) placing all of the plurality of switches associated with one of the other three of the four legs in the output circuit in a conducting state so that current is conducted through that one leg and the leg made conducting in step (a);

(c) monitoring a parameter associated with the legs made conducting in steps (a) and (b) to ensure that current does flow through the two legs made conducting in steps (a) and (b) from the energy storage capacitor; and (d) repeating steps (a)–(c) for the other two of the four legs in the output circuit.

6. The method of claim 5, wherein the parameter is a voltage across the energy storage capacitor.

7. The method of claim 5, further comprising the step of charging the energy storage capacitor to a testing voltage.

8. The method of claim 5, further comprising the step of providing a warning indication to a user of the external defibrillator if current does not flow through legs made conducting in steps (a) and (b).

9. In an external defibrillator, a method of verifying the integrity of an output circuit during application of a multiphasic defibrillation pulse to a patient, the output circuit comprising a plurality of switches coupled to an energy storage capacitor to allow the energy storage capacitor to be electrically coupled to the patient for application of the defibrillation pulse, the method comprising the steps of:

(a) placing some of the plurality of switches in a conductive state to start application of the first phase of the multiphasic defibrillation pulse;

(b) monitoring an elapsed time from the start of the first phase of the multiphasic defibrillation pulse;

(c) measuring a parameter related to the energy flow from the capacitor to the patient at a predetermined elapsed time during the application of the first phase of the multiphasic defibrillation pulse;

(d) before beginning the next phase of the multiphasic defibrillation pulse, verifying the integrity of the output circuit by comparing the measured parameter with a range of expected parameters based on an impedance range of a patient to determine if the measured parameter falls within the expected range; and (e) providing a warning to the user if the measured parameter does not fall within the expected range.

10. The method of claim 9, wherein the measured parameter is a voltage across the energy storage capacitor.

11. In an external defibrillator, a method of verifying the integrity of an output circuit during application of a multiphasic defibrillation pulse to a patient, the output circuit comprising a plurality of switches coupled to an energy storage capacitor to allow the energy storage capacitor to be electrically coupled to the patient for application of the defibrillation pulse, the method comprising the steps of:

(a) placing some of the plurality of switches in a conductive state to start application of the first phase of the multiphasic defibrillation pulse;

(b) monitoring a parameter related to the energy flow from the capacitor to the patient;

(c) during application of the first phase of the multiphasic defibrillation pulse, measuring an elapsed time when the monitored parameter reaches a predetermined level;

(d) before beginning the next phase of the multiphasic defibrillation pulse, verifying the integrity of the output circuit by comparing the elapsed time with a range of expected times based on an impedance range of a patient to determine if the elapsed time falls within the expected range; and (e) providing a warning to the user if the elapsed time does not fall within the expected range.

12. The method of claim 11, wherein the monitored parameter is a voltage across the energy storage capacitor.

13. A method of compensating for a malfunctioning output circuit in an external defibrillator, the output circuit having two legs coupled to one lead of an energy storage capacitor and two legs coupled to the other lead of the energy storage capacitor for application of a multiphasic defibrillation pulse to a patient, the method comprising the steps of:

(a) testing each of the legs in the output circuit to identify if each leg is operational or has failed;

(b) applying a multiphasic defibrillation pulse to the patient if all of the legs in the output circuit are operational; and (c) applying a monophasic defibrillation pulse to the patient if at least one of the legs in the output circuit has failed and a conductive path is present through one of the legs coupled to one lead of the energy storage capacitor, the patient, and one of the legs coupled to the other lead of the energy storage capacitor.

14. The method of claim 13, further comprising the step of charging the energy storage capacitor to a higher voltage if a monophasic defibrillation pulse is to be applied to the patient.

15. The method of claim 13, wherein the step of testing each of the legs in the output circuit occurs prior to application of the defibrillation pulse.

16. The method of claim 13, further comprising the step of providing a warning indication to a user if at least one of the legs in the output circuit has failed.

17. The method of claim 13, wherein steps (a)–(c) are repeated each time a defibrillation pulse is applied to a patient.

* * * * *